(12) United States Patent
Weissert et al.

(10) Patent No.: US 8,557,959 B2
(45) Date of Patent: Oct. 15, 2013

(54) ALLELE AND ISOTOPE-SPECIFIC INTERVENTION ON MHC CLASS II MOLECULES ASSOCIATED WITH AUTOIMMUNE DISEASES BY MEANS OF PEPTIDES

(75) Inventors: Robert Weissert, Nyon (CH); Karl-Heinz Wiesmueller, Herrenberg (DE); Katrien L. De Graaf, Nyon (CH)

(73) Assignee: Merck Serono S.A., Coinsins (Vaud) (CH)

( * ) Notice: Subject to any disclaimer, the term of this patent is extended or adjusted under 35 U.S.C. 154(b) by 374 days.

(21) Appl. No.: 12/746,098

(22) PCT Filed: Dec. 3, 2008

(86) PCT No.: PCT/EP2008/010230
§ 371 (c)(1),
(2), (4) Date: Nov. 8, 2010

(87) PCT Pub. No.: WO2009/071276
PCT Pub. Date: Jun. 11, 2009

(65) Prior Publication Data
US 2011/0053840 A1 Mar. 3, 2011

(30) Foreign Application Priority Data
Dec. 3, 2007 (DE) .......................... 10 2007 059 924

(51) Int. Cl.
*A61K 38/08* (2006.01)
*C07K 1/00* (2006.01)

(52) U.S. Cl.
USPC ....................................................... 530/328

(58) Field of Classification Search
None
See application file for complete search history.

(56) References Cited

FOREIGN PATENT DOCUMENTS
WO WO9420127 A1 9/1994

OTHER PUBLICATIONS

Markovic-Plese et al (Journal of Immunology 1995, 155: 982-992).*
Hansen et al (Tissue Antigens, 2011: 77(3): 229-234, abstract).*
Wekerle et al (Nature Med. 2012, 18(1): 66-70).*
Rammensee et al (MHC Ligands and Peptide Motifs, Landes Bioscience, 1997, Springer, NY, pp. 315 and 362).*
Kurane et al (J. Gen. Virol. 1995, 76: 2243-2249).*
Duyar et al.,"Peptide motif for the rat MHC class II molecule RT1.Da: similarities to the multiple sclerosis-associated HLA-DRB1*1501 molecule," Immunogenetics, 2005, pp. 69-76, vol. 57, No. 1-2.
De Graaf et al.,"Characterization of the encephalitogenic immune response in a model of multiple sclerosis," European Journal of Immunology, 2008, pp. 299-308, vol. 38, No. 1.
De Graaf et al.,"MHC class II isotype and allele-specific attenuation of experimental autoimmune encephalomyelitis," Journal of Immunology, 2004, pp. 2792-2802, vol. 173, No. 4.
Weissert et al., "MHC Class II-Regulated Central Nervous System Autoaggression and T Cell Responses in Peripheral Lymphoid Tissues Are Dissociated in Myelin Oligodendrocyte Glycoprotein-Induced Experimental Autoimmune Encephalomyelitis", Journal of Immunology, 166:7588-7599 (2001).
Wu et al., "cDNA Cloning and Sequencing Reveals that the Electronically Constant DR Beta 2 Molecules as Well as the Variable DR Beta 1 Molecules, From HLA-DR2 Subtypes Have Different Amino Acid Sequences Including a Hypervariable Region for a Functionally Important Epitope.", Journal of Immunology, 138(9):2953-2959 (1987).

* cited by examiner

*Primary Examiner* — Gerald R Ewoldt
*Assistant Examiner* — Marianne Dibrino
(74) *Attorney, Agent, or Firm* — Browdy and Neimark, PLLC

(57) ABSTRACT

The present invention relates to a peptide for the treatment or prophylaxis of an autoimmune disease, a nucleic acid molecule coding for said peptide, a pharmaceutical composition comprising the peptide and/or the nucleic acid molecule, and to a method for the treatment and/or prophylaxis of an autoimmune disease.

1 Claim, 3 Drawing Sheets

Figure 1:
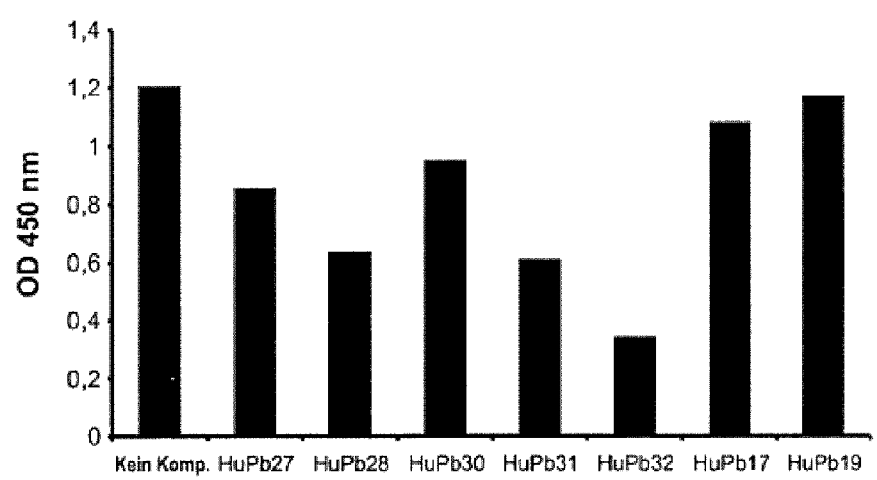

ALLELE AND ISOTOPE-SPECIFIC INTERVENTION ON MHC CLASS II MOLECULES ASSOCIATED WITH AUTOIMMUNE DISEASES BY MEANS OF PEPTIDES

The present invention relates to a peptide for the treatment or prophylaxis of an autoimmune disease, a nucleic acid molecule coding for this peptide, a pharmaceutical composition comprising the peptide and/or the nucleic acid molecule, and to a method for the treatment and/or prophylaxis of an autoimmune disease.

Autoimmune diseases, also called diseases of autoagression, are diseases that are caused by autoantibodies or self-reactive T cells. Autoimmunity is based on a specific, adaptive immune response to endogenous antigens. It can be understood as the result of a breakdown of the tolerance toward endogenous substances and/or of a defective control- and regulating mechanism of the immune system. Besides environmental factors, genetic factors are counted among the causes of autoimmune diseases, such as for example the major histocompatibility complex (MHC) genotype.

Multiple sclerosis (MS) is one prominent example of an autoimmune disease. This inflammatory autoimmune disease of the central nervous system, which leads to a neurodegeneration, is characterized by a focal degeneration of the myelin sheaths. The nerve pathways themselves also become destroyed. The disease progresses chronically in the form of flare-ups that are often spaced far apart in time, frequently with regressions of the clinical symptoms, but it may also develop slowly continuously progredient. The symptoms are very varied—depending on which affected part of the nervous system is breaking down—and may involve, e.g. visual disturbances, double vision caused by paralysis of the eye muscles, tremors, dizzy spells, muscle weakness, paralyses, incontinence, sensibility and speech disturbances, mental changes. The disease usually starts between the ages of 20 and 40; women are affected more often than men. In comparison with other parts of the world, multiple sclerosis occurs with particular frequency in Northern Europe and North America and is one of the most frequently occurring neurological diseases in Central Europe, with an incidence of approximately 1 per 1000 inhabitants per year.

Like most of the other autoimmune diseases, MS as a complex genetic disease is associated with certain allelic variants of MHC class II isotypes. In the Caucasian population, the strongest association exists with the HLA-DR15 haplotype, i.e. DRB1*1501, DRB5*0101, DQA1*0102 and DQB1*0602. Recently published studies indicate that HLA-DRB1*1501 presents the strongest genetic risk factor for developing MS. The association of the MHC class II molecules with the disease can probably be attributed to the fact that these molecules present fragments of autoantigens on autoreactive T cells that then trigger the disease in the central nervous system.

There currently is no cure for MS. However, some medicaments are available that can slow down the progression of MS and alleviate symptoms that have already occurred. Administering high-dose corticosteroids during an acute flare-up, for example, can reduce the inflammatory response in the central nervous system and lead to an improvement of the symptoms. Immunosuppressants or immunomodulators, which suppress the immune system or alter the immune response, are used in the context of long-term therapy. One difficulty with this principle of action is that an overly unspecific alteration of the immune system can lead to higher rates of infection and cancer. In the context of symptomatic therapy, medicaments are used that alleviate the symptoms that are frequently observed in patients, such as chronic fatigue and lack of energy, the so-called fatigue syndrome, the spacitity and voiding disorders, but that do not treat the causes.

Against that background, the invention is based on the aim of providing a composition that causally intervenes with the pathology of autoimmune diseases and thus permits a targeted treatment or prophylaxis of autoimmune diseases such as, for example, multiple sclerosis.

This aim is achieved by providing a peptide that is made up in such a way that it can bind with high affinity to the human MHC class II molecule HLA-DR2b.

The aim of the invention is thereby fully achieved.

The inventors have conducted studies on MCH-congenic rats, HLA-DR2b-transfected cell lines and myelin basic protein (MBP) specific T cell lines and HLA-DR2b-transgenic mice. The data generated in vivo demonstrated that the application of the high-affinity peptides according to the invention can suppress and/or delay the development of an experimentally induced MS-like autoimmune disease, the experimental autoimmune encephalomyelitis (EAE). The in vitro experiments show that the peptides bring about a reduction in the T cell proliferation of human MBP-specific autoreactive T cells. In HLA-DR2b-transgenic mice the peptides lead to a reduction in the severity of the disease. The inventors therefore are providing for the first time a composition that is able to selectively bind allele- and isotype-specifically to the MHC class II molecule HLDR2b, and in this way interferes with the MHC class II presentation of autoantigens.

The effectiveness of the peptide according to the invention in experimental autoimmune encephalomyelitis recognized by the inventors was surprising and would not have been expected. It has been described by de Graaf et al. (2004) MHC class II isotype- and allele-specific attenuation of experimental autoimmune encephalomyelitis, J. Immunol. 173, 2792-2802, that peptides can be provided that bind isotype- and allele-specifically to the rat MHC class II molecules RT1.B and RT1.D and can, in the process, attenuate the experimental autoimmune encephalomyelitis.

However, it was not possible to conclude from the studies performed for rats that corresponding peptides can be generated that are able to bind with high affinity to the human MHC class II molecule HLA-DR2b, because HLA-DR2b in the human and RT1.B and RT1.D in the rat are structurally different. Moreover, the genetic make-up of the MHC genome and that of the Non-MHC genome are different from each other, and so are the immune systems of the rat, mouse and human. For that reason the in vitro data that were obtained by the inventors with human T cells and antigen-presenting cells were particularly surprising.

The synthesis of the peptides according to the invention is carried out using methods that are known to a person skilled in the art, which are described in standard textbooks; cf. John Howl (Pub.) (2005), Peptide Synthesis and Applications (Methods in Molecular Biology), Human Press; 1st edition. Some of these processes run fully automatically, such that a multitude of peptides with randomized amino-acid sequences can be prepared within a very short amount of time. Alternatively, it is also possible to fall back on commercially available peptide libraries. The binding affinity of the synthesized peptide according to the invention for HLA-DR2b can be measured, for example, using a competitive fluorescence-based ELISA on purified HLA-DR2b molecules, as described in the examples. The specific embodiment of the peptide therefore is prepared according to standard methods and does not require any unreasonable experimentation.

The human MHC class II molecule HLA-DR2b has been described, for example by Wu et al. (1987), cDNA cloning and sequencing reveals that the electrophoretically constant DR β-2 molecules as well as the variable DR β-1 molecules, from HLA-DR2 subtypes have different amino acid sequences including a hypervariable region for a functionally important epitope, J. Immunol. 138 (9), pages 2953-2959. The content of this publication has been made part of the present application. The amino acid sequence of the human HLA-DR2b is published in the NCBI database and shown in the appended sequence protocol under SEQ ID No. 26.

It is preferred in this context when the peptide according to the invention has an $IC_{50}$ value for binding to HLA-DR2b that is approximately ≤0.1 µM, preferably approximately ≤0.01 µM, more preferably approximately ≤0.002 µM and most preferably approximately ≤0.001 µM.

This measure has the advantage that the peptides bind to HLA-DR2b with particularly high affinity, thereby ensuring high efficacy in the therapy and/or prophylaxis of autoimmune diseases. The $IC_{50}$ value indicates the concentration of an inhibitor—in the present case of the peptide according to the invention—that is required in order to inhibit an enzyme, a cell, a cell receptor, a microorganism—in the present case the HLA-DR2b molecule—in general: target structures—in vitro by 50%.

The peptide according to the invention preferably has fewer than 20 amino acids, more preferably fewer than 15 amino acids, more preferably fewer than 10 amino acids and most preferably 9 amino acids, or consists of the number of amino acids mentioned above.

This measure has the advantage that the peptide, due to the short length thereof, is not only particularly stable, but can also be synthesized and formulated pharmaceutically easily and cost-effectively.

According to the invention, it is furthermore preferred when the peptide inhibits the antigen-presenting ability of HLA-DR2b.

It is known that by the presentation of antigens, in particular autoantigens, by the human MHC class II molecule HLA-DR2b, destructive autoreactions of the immune system are triggered on T cells. By inhibiting the presentation of antigens of endogenous origin, the autoimmune response is inhibited according to the invention in a specific manner, and the progredience of the disease is thereby slowed down or even stopped, if applicable.

In this context it is preferred when the peptide according to the invention exhibits immunomodulatory activity, which preferably is a therapeutic effect against an autoimmune disease.

In the context of the present invention, "immunomodulatory activity" refers to the fact that the peptide, after application into a patient affected by or susceptible to an autoimmune disease, leads to an alteration of the autoimmune disease by way of influencing the immune response. This immunomodulatory activity preferably is a therapeutic effect against an autoimmune disease.

This measure has the advantage that a kind of peptide is provided that is suitable for a targeted therapeutic intervention into the pathology of an autoimmune disease.

It is preferred in this context when the immunomodulatory activity is a therapeutic effect against experimental autoimmune encephalomyelitis (EAE) or multiple sclerosis (MS).

With this improvement a peptide is provided that has therapeutic effect against one of the most problematic and most important autoimmune diseases.

According to one improvement, the peptide according to the invention has the following structure:

NX1-X2-X3-X4-X5-X6-X7-X8-X9C (SEQ ID NO:27)
where N denotes the N-terminal end and C denotes the C-terminal end;
where '-' denotes a peptide bond;
where X1 denotes an amino acid that is selected from the group consisting of: leucine, valine, isoleucine, methionine, phenylalanine, aspartic acid;
where X2 denotes an amino acid that is selected from the group consisting of isoleucine, leucine, valine;
where X3 denotes an amino acid that is selected from the group consisting of: leucine, isoleucine, methionine, tyrosine, aspartic acid;
where X4 denotes an amino acid that is selected from the group consisting of: tyrosine, tryptophan, isoleucine;
where X5 denotes an amino acid that is selected from the group consisting of: tyrosine, phenylalanine, isoleucine, tryptophan;
where X6 denotes an amino acid that is selected from the group consisting of: tyrosine, serine, asparagine;
where X7 denotes an amino acid that is selected from the group consisting of tyrosine, serine, asparagine, phenylalanine;
where X8 denotes an amino acid that is selected from the group consisting of: tyrosine, tryptophan, leucine, serine, and
where X9 denotes an amino acid that is selected from the group consisting of: leucine, isoleucine, valine, proline, tyrosine, phenylalanine, aspartic acid.

The inventors have measured 171 randomized nonapeptides for their ability to bind with high affinity to a purified HLA-DR2b molecule. From the result of these measurements the above consensus sequence was determined. By providing the amino acids mentioned at respective positions $X_i$-$X_9$ it is ensured that the kind of peptides are obtained that are able to bind with high affinity to the human MHC class II molecule HLA-DR2b and therefore are of particular therapeutic significance.

It is preferred in this context when the N-terminal end in the peptide according to the invention is acetylated and the C-terminal end is amidated.

The reason for this is that it is known that for filling the peptide binding groove of the MHC-II-molecules, peptides are preferably used that have a length of nine amino acids, but longer peptides can enter into more stable bonds. Through amidation and acetylation two additional amino acids are imitated, thereby also stabilizing the peptide in the binding groove.

According to one preferred improvement, the peptide according to the invention has an amino acid sequence that is selected from the group consisting of: SEQ ID No. 1 to SEQ ID No. 15.

With this measure a peptide is already provided that has been shown in the experiments conducted by the inventors to have a particularly high affinity towards HLA-DR2b and thus be therapeutically particularly effective. The stated amino acid sequences can, of course, N-terminally or C-terminally have additional amino acid sequences without this having any significant impact on the therapeutic effect and on the ability of the peptide to bind with high affinity to the human MHC class II molecule HLA-DR2b. It is solely the continuous sequence of the new amino acids within a peptide that ensures the binding to HLA-DR2b and therefore the therapeutic effect of the peptide.

Against that background the present invention also has as a subject matter a peptide having an amino acid sequence identity with the peptide mentioned above, or with one of the sequences SEQ ID No. 1 to SEQ ID No. 15, of approximately 50%, more preferably of approximately 60%, more preferably of approximately 70%, more preferably of approximately 80%, more preferably of approximately 90%, more preferably of approximately 95%, more preferably of approximately 99% and most preferably of approximately 100%.

It is known that peptides with a sufficiently high amino acid sequence identity have comparable activities. For example, the exchange of one amino acid having certain chemical properties (e.g. aspartic acid) against another amino acid having similar chemical properties (e.g. glutamic acid) does not result in a loss of the biological activity of the peptide. Such peptides with modified, sufficiently identical or homologous amino acid sequences also utilize the properties of the peptides according to the invention and are covered within the scope of the invention. Sequence identities are easy to determine with the aid of standard software available to a person skilled in the art. One example for such a software is the SEM Alignment Tool for Protein Sequences, expasy.org/tools/sim-prot.html.

Against that background the present invention also has as a subject matter a peptide having an amino acid sequence identity with the aforementioned peptide, or with one of the sequences SEQ ID No. 1 to SEQ ID No. 15, of approximately 50%, more preferably of approximately 60%, more preferably of approximately 70%, more preferably of approximately 80%, more preferably of approximately 90%, more preferably of approximately 95%, more preferably of approximately 99% and most preferably of approximately 100%.

Such peptides, too, have a sufficiently high affinity towards the human MHC class II molecule HLA-DR2b and are therefore suitable for the treatment and/or prophylaxis of autoimmune diseases.

The activity of such a peptide can easily be determined in the model developed by the inventors and described in the examples.

According to a preferred improvement, the peptide according to the invention comprises a medicament against MS that is preferably selected from the group consisting of: corticosteroid; interferon, preferably Betaferon®, Avonex®, Rebif®; glatiramer acetate, preferably Copaxone®; azathioprine, preferably Imurek®; natalizumab, preferably Antegren®/Tysabri®; mitoxantrone, preferably Ralenova®; cyclophosphamide, preferably Endoxan®; methotrexate, preferably Metex 7,5®; immunoglobulin, preferably Gamunex® 10%, Octagam®.

This measure has the advantage that the therapeutic and/or prophylactic effect of the peptide according to the invention is increased even further. By combining the peptide with a conventional medicament against MS, various modes of action are provided that lead to a particularly efficient treatment of a patient affected by MS.

Against that background the present invention has as another subject matter the use of the peptide according to the invention for producing a medicament for the therapeutic and/or prophylactic treatment of an autoimmune disease.

A further subject matter of the present invention is a nucleic acid molecule, preferably an expression vector coding for the peptide according to the invention.

A further subject matter of the present invention relates to a pharmaceutical composition comprising the peptide according to the invention and a pharmaceutically acceptable carrier.

Pharmaceutically acceptable carriers are described, for example, in Rowe et al. (2006), Handbook of Pharmaceutical Excipients, Pharmaceutical Press and American Pharmacists Assoc., 5$^{th}$ Edition, and in Bauer et al. (1999) Lehrbuch der Pharmazeutischen Technologie, Wissenschaftliche Verlagsgesellschaft mbH, Stuttgart. The content of the above publications is incorporated into the present application by reference.

The invention additionally has as a subject matter a method for the treatment or prophylaxis of an autoimmune disease preferably selected from the group consisting of: multiple sclerosis (MS), experimental autoimmune encephalomyelitis (EAE), rheumatoid arthritis, diabetes mellitus type I, myasthenia gravis, in a living being of preferably human origin, the MHC class II molecule preferably being of the type HLA-DR2b, comprising the following steps: (1) selective allele- and isotype-specific inhibition of the presentation of antigens by MHC class II molecules in the living being, and (2) optionally repeating of step 1.

In this context, the inhibition of the presentation of antigens is preferably effected by administration of a peptide that is able to bind with high affinity to the human class II molecule HLA-DR2b. It is preferred in this context when the peptide according to the invention is used as the peptide. Alternatively, the inhibition of the presentation of antigens by MHC class II molecules can be effected by administration of the nucleic acid molecule according to the invention and/or the pharmaceutical composition according to the invention.

The features presented above and those to be explained below can, of course, be used not only in the combination indicated in each case, but also in other combinations or by themselves, without leaving the scope of the present invention.

The invention will now be explained in more detail on the basis of examples, from which additional features and advantages will become apparent. The examples are strictly illustrative and are not intended to limit the invention.

Reference is made to the appended drawings. In these drawings,

FIG. 1 shows the MBP-85-99 induced secretion of IL-2 by the HLA-DR2b peptides according to the invention. L466 cells and 08073 cells, which were transfected with HLA-DR2b, were co-incubated in the presence of 1 µg/ml MBP 85-99 and 10 µg/ml of various HLA-DR2b peptides; "kein Komp."=no peptide according to the invention in the batch. After 24 hours the supernatant was collected and the amount of IL-2 present in the supernatant was measured in a mouse-specific IL-2-ELISA.

Figure 2:
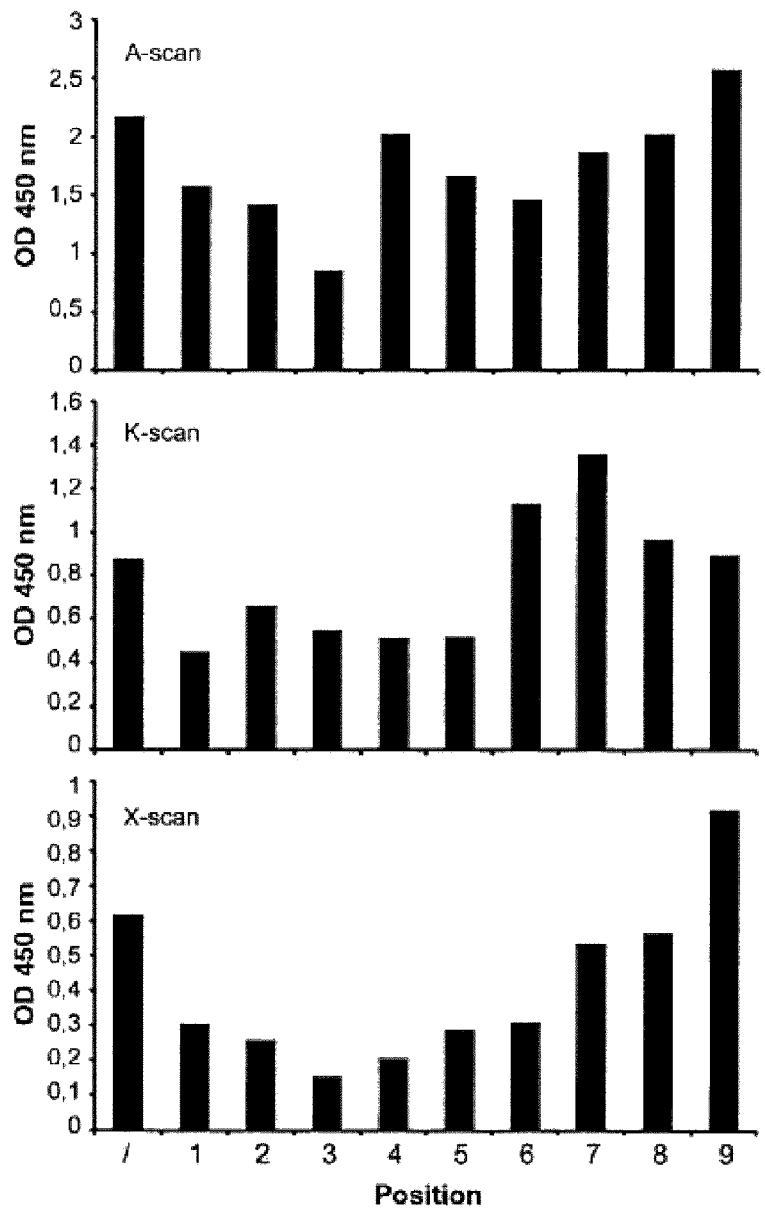

FIG. 2 shows the inhibitory capacity of A-, K- and X-substituted HuP$_b$28 variants. L466 cells and 08073 cells that were transfected with HLA-DR2b were co-incubated in the presence of 1 µg/ml MBP 85-99 and 10 µg/ml of the HuP$_b$28-variants. After 24 hours the supernatant was collected and the amount of IL-2 present in the supernatant was measured using a mouse-specific IL-2-ELISA.

Figure 3:
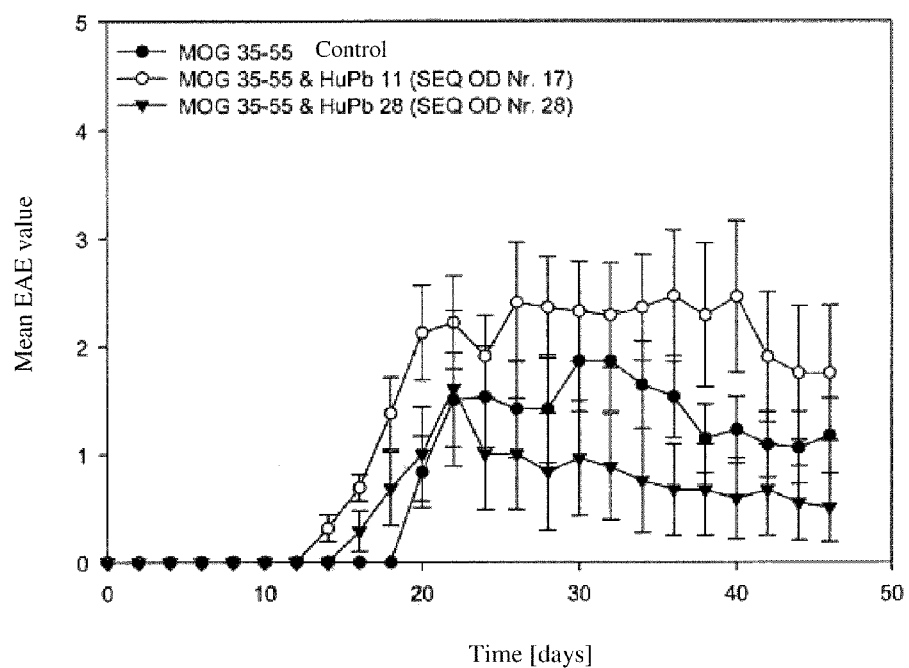

FIG. 3 shows the results of a co-immunization experiment. DR2b mice were immunized with the MOG 35-55 peptide in CFA (n=8) or co-immunized with MOG 35-55 and the HuP$_b$11 peptide (SEQ ID No. 17) (n=8) or MOG 35-55 and HuP$_b$28 peptide (SEQ ID No. 9) (n=9). Pertussis toxin (PTX) was administered i.p. on days 0 and 2. The mice were measured daily for EAE and weighed. The co-administration of the HuP$_b$28 peptide (SEQ ID No. 9; -▼-) leads to a reduction in the sum value (p<0.05).

1. MATERIALS AND METHODS 1.1 Peptide Libraries and Peptides

Libraries with synthetically acetylated nonapeptide amides and also defined acetylated nonapeptide amides and biotinylated peptide amides were prepared by fully automated solidphase peptide synthesis using 9-fluorenylmetoxycarbonyl-tert-buty (Fmoc-tWu) chemistry and analyzed by means of HPLC- and electron spray ionization mass spectroscopy. Biotinylated CLIP peptide 97-120 (LPKSAK-PVSPMRMATPLLMRPSMD (SEQ ID NO:28)) was obtained by elongating the peptide with two spacer amino acids, followed by biotin using a coupling method.

1.2 Purification of DR2b Molecules and Peptide-Binding Assays

DR2b molecules were purified from L cells that had been co-transfected with HLA-DRA and HLA-DRB1*1501, by affinity chromatography using the HLA-DR-specific L243 antibody, as described in Weissert et al. (2001), MHC class II-regulated central nervous system autoaggression and T cell responses in peripheral lymphoid tissues are dissociated in myelin oligodendrocyte glycoprotein-induced experimental autoimmune encephalomyelitits, J. Immunol. 166, 7588-7599. The above publication is incorporated into the present application by reference. The binding assays were performed with a competitive ELISA based on a dissociation-enhanced lanthanide fluoroimmunoassay (Wallac, Turku, Finland). For the competitive ELISA, a 50 nM solution of DR2b molecules was incubated for 48 hours at 37° C. with 50 nM biotinylated CLIP 97-120 in the presence of 250 nM acetylated nonapeptide amide sublibrary or with various concentrations of competitor peptides ranging from 1 nM to 100 µM. The $IC_{50}$ of a peptide was defined as the concentration of peptide that was required for a 50% inhibition of the binding of the tracer peptide.

1.3 Blocking of IL-2 Secretion by High-Affinity Ligands for DR2b

A T cell hybridoma (08073), which expresses the T cell receptor that is specific for MBP 85-99, which is presented by HLA-DR2b, was provided. After stimulation with MBP 85-99, presented by HLA-DR2b-transfected L466 cells, the 08073 cells secreted significant amounts of IL-2. $5 \times 10^4$ 08073 cells were co-incubated for 24 hours with $5 \times 10^4$ HLA-DR2b-transfected L466 cells in RPMI medium (Invitrogen, Pailey, United Kingdom)/2% FCS (PAA, Linz, Austria)/100 U/ml penicillin, 100 µg/ml streptomycin, 2 mM glutamine (all from Invitrogen) in the presence of 1 µg/ml MBP 85-00 with or without high-affinity peptides (10 µg/ml). The amounts of IL-2 that were secreted in the supernatant were detected using a mouse-IL-2-specific ELISA (BD Biosciences Pharmingen, San Diego, Calif., United States of America).

1.4 Mice and Induction of EAE

HLA-DR2b-transgenic female mice (Rich et al., (2004): Myelin oligodendrocyte glycoprotein-35-55 peptide induces severe chronic experimental autoimmune encephalomyelitis in HLA-DR2-transgenic mice, Eur. J. Immunol. 34, 1251-1261, at the ages of 8-14 weeks were immunized using 300 µg myelin oligodendrocyte glycoprotein-35-55-peptide (MOG 35-55) in CFA, or co-immunized using 300 µg MOG 35-55 and 200 µg of $HuP_b28$ peptide (SEQ ID No. 9) or $HuP_b11$ peptide (SEQ ID No. 17) in CFA. On day 0 and on day 2, 400 ng pertussis toxin (PTX) were administered p.i. i.p. The mice were observed for up to 46 days and clinically classified. The following classifications were used: 0, no disease; 1, weakness or paralysis of the tail; 2, weakness of the hind legs; 3, paralysis of the hind legs; 4, paralysis of the front and hind legs; 5, moribund or death caused by disease.

2. RESULTS AND DISCUSSION 2.1 Preparation of an Activity Pattern for the MS-Associated HLA-DR2b Molecules In the first step, an activity pattern was prepared for the HLA-DR2b molecule in such a way that the effect of each individual amino acid was studied at each position of the peptide binding pocket of the MHC class II molecule. This was done in such a way that the affinity of 171 nonapeptide (9 sequence positions×19 amino acids, excluding cysteine, see Table I) was measured for purified HLA-DR2b molecules using a competitive fluorescence-based ELISA.

TABLE I

Schematic presentation of the synthetic acetylated nonapeptide amide libraries

| | | | |
|---|---|---|---|
| Ac-XAXXXXXXX-$NH_2$ | Ac-XDXXXXXXX-$NH_2$ | ... | Ac-XYXXXXXXX-$NH_2$ |
| Ac-AXXXXXXXX-$NH_2$ | Ac-DXXXXXXXX-$NH_2$ | ... | Ac-YXXXXXXXX-$NH_2$ |
| ... | ... | ... | ... |
| Ac-XXXXXXXXA-$NH_2$ | Ac-XXXXXXXXD-$NH_2$ | ... | Ac-XXXXXXXXY-$NH_2$ |

The resulting activity pattern is shown in Table II below:

TABLE II

Relative impact of the defined amino acid residues on the binding activity of peptides for the purified DR2b molecules. This table shows relative competition values that were calculated in such a way that the competition value obtained for a certain nonapeptide sublibrary was divided by the competition value obtained for a completely randomized nonapeptide sublibrary (Ac—$X_9$—$NH_2$) obtained on the same plate with 96 depressions.

| | | Position | | | | | | | | | | | | | | | | | |
|---|---|---|---|---|---|---|---|---|---|---|---|---|---|---|---|---|---|---|---|
| | | 1 | | 2 | | 3 | | 4 | | 5 | | 6 | | 7 | | 8 | | 9 | |
| High affinity | L | 2.36 | I | 2.33 | L | 2.07 | Y | 3.31 | Y | 4.10 | Y | 2.79 | Y | 2.94 | Y | 2.76 | L | 3.81 | |
| | V | 2.20 | L | 2.21 | I | 1.94 | W | 2.18 | F | 2.00 | S | 2.02 | S | 2.58 | W | 1.94 | I | 1.97 | |
| | I | 2.08 | V | 1.71 | M | 1.83 | I | 2.03 | I | 1.76 | N | 1.71 | N | 1.58 | L | 1.78 | V | 1.80 | |
| | M | 2.01 | | | | | Y | 1.66 | | | W | 1.45 | | | F | 1.50 | S | 1.43 | P | 1.77 |
| | F | 1.69 | | | | | | | | | | | | | | | | | Y | 1.46 |
| | | | | | | | | | | | | | | | | | | | F | 1.41 |
| Moderate affinity | Y | 1.31 | M | 1.26 | F | 1.24 | M | 1.33 | S | 1.19 | W | 1.35 | A | 1.31 | N | 1.06 | A | 1.38 | |
| | N | 1.00 | R | 1.18 | V | 1.10 | R | 1.26 | L | 0.90 | G | 1.11 | G | 1.03 | P | 1.06 | M | 1.27 | |
| | R | 0.94 | | | | | R | 1.07 | F | 1.20 | V | 0.80 | A | 0.92 | M | 0.93 | H | 0.89 | N | 0.91 |
| | T | 0.92 | | | | | T | 0.90 | V | 1.14 | A | 0.77 | K | 0.90 | T | 0.88 | K | 0.86 | K | 0.84 |
| | Q | 0.85 | | | | | N | 0.78 | H | 0.75 | T | 0.75 | R | 0.89 | W | 0.86 | R | 0.79 | W | 0.77 |
| | A | 0.84 | | | | | A | 0.71 | | | M | 0.73 | L | 0.89 | L | 0.83 | I | 0.74 | H | 0.75 |
| | S | 0.82 | | | | | | | | | M | 0.84 | I | 0.80 | T | 0.70 | T | 0.70 | | |

TABLE II-continued

Relative impact of the defined amino acid residues on the binding activity of peptides for the purified DR2b molecules. This table shows relative competition values that were calculated in such a way that the competition value obtained for a certain nonapeptide sublibrary was divided by the competition value obtained for a completely randomized nonapeptide sublibrary (Ac—$X_9$—$NH_2$) obtained on the same plate with 96 depressions.

| | | Position | | | | | | | | | | | | | | | | |
|---|---|---|---|---|---|---|---|---|---|---|---|---|---|---|---|---|---|---|
| | | 1 | | 2 | | 3 | | 4 | | 5 | | 6 | | 7 | | 8 | | 9 |
| | H | 0.81 | | | | | | | | P | | 0.83 | P | 0.78 | V | 0.70 | | |
| | K | 0.74 | | | | | | | | V | | 0.76 | | | | | | |
| Low | E | 0.55 | Q | 0.67 | S | 0.68 | G | 0.57 | H | 0.58 | H | 0.49 | V | 0.63 | M | 0.69 | Q | 0.60 |
| affinity | G | 0.51 | K | 0.58 | H | 0.60 | T | 0.57 | N | 0.57 | D | 0.47 | K | 0.53 | G | 0.68 | S | 0.53 |
| | P | 0.50 | F | 0.58 | W | 0.55 | Q | 0.54 | K | 0.47 | Q | 0.45 | H | 0.47 | Q | 0.54 | G | 0.53 |
| | W | 0.33 | T | 0.58 | G | 0.52 | K | 0.54 | P | 0.34 | I | 0.43 | Q | 0.31 | A | 0.47 | D | 0.35 |
| | D | 0.19 | Y | 0.55 | Q | 0.45 | N | 0.46 | R | 0.22 | T | 0.28 | D | 0.28 | D | 0.43 | E | 0.14 |
| | | | A | 0.45 | P | 0.25 | L | 0.36 | D | 0.15 | E | 0.26 | R | 0.21 | E | 0.29 | R | 0.05 |
| | | | G | 0.40 | K | 0.16 | D | 0.27 | G | 0.13 | F | 0.23 | E | 0.05 | F | <0.01 | | |
| | | | H | 0.34 | E | 0.07 | A | 0.27 | Q | 0.02 | | | | | | | | |
| | | | E | 0.33 | D | 0.06 | E | 0.27 | E | <0.01 | | | | | | | | |
| | | | D | 0.31 | | | S | 0.20 | | | | | | | | | | |
| | | | S | 0.20 | | | P | 0.15 | | | | | | | | | | |
| | | | W | 0.14 | | | | | | | | | | | | | | |
| | | | P | 0.09 | | | | | | | | | | | | | | |
| | | | N | 0.05 | | | | | | | | | | | | | | |

Negatively charged amino acids are generally disadvantageous for the binding capacity. Large hydrophobic residues, in contrast, tend to enhance the binding. The aromatic polar amino acid tyrosine (Y) enhances the affinity in all positions, except for the second position. Other aromatic and polar amino acids, such as for example serine (S) and threonine (T), likewise are disadvantageous in this position. The presence of large aliphatic hydrophobic side chains in the first three positions enhances the affinity. Positions 4 and 5, in contrast, are preferably occupied by aromatic amino acids. At positions 6 and 7 the polar amino acids serine (S) and asparagine (N) enhance the binding capacity, whereas the presence of aliphatic side chains in these positions is rather unfavorable. Significantly enough, phenylalanine (F) has a strong negative effect on the affinity if it is present at position 6, whereas it enhances the affinity if it is present at position 7. Lastly, positions 8 and 9 are preferably occupied by aromatic and aliphatic hydrophobic residues.

2.2 Test of the Activity Pattern Established for the HLA-DR2b Molecule

Two sets of peptides were synthesized for the purpose of validating the HLA-DR2b activity pattern. The first set of peptides consists of randomizedly selected combinations of disadvantageous amino acids for each of the nine positions ($HuP_b10$-$HuP_b19$), whereas the second set of peptides was prepared using randomized combinations of advantageous amino aids ($HuP_b20$-$HuP_b34$); cf. Table III.

TABLE III $IC_{50}$ values of the acetylated nonapeptide amides for binding to HLA-DR2b molecules. Only small quantities of the peptides $HuB_b6$, $HuP_b7$, $HuP_b12$, $HuP_b13$, $HuP_b16$ and $HuP_b25$ were obtained following the synthesis. Therefore no $IC_{50}$ values could be determined for these peptides.

| Affinity | Peptide | Sequence | $IC_{50}$ (µM) | SEQ ID No. |
|---|---|---|---|---|
| Low-affinity ligands | $HuP_b10$ | WPLPLLEER | 33.9 | 16 |
| | $HuP_b11$ | WGLPEHLER | >100 | 17 |
| | $HuP_b12$ | GWLSELEDR | — | 18 |

TABLE III-continued $IC_{50}$ values of the acetylated nonapeptide amides for binding to HLA-DR2b molecules. Only small quantities of the peptides $HuB_b6$, $HuP_b7$, $HuP_b12$, $HuP_b13$, $HuP_b16$ and $HuP_b25$ were obtained following the synthesis. Therefore no $IC_{50}$ values could be determined for these peptides.

| Affinity | Peptide | Sequence | $IC_{50}$ (µM) | SEQ ID No. |
|---|---|---|---|---|
| | $HuP_b13$ | PFPAPTREG | — | 19 |
| | $HuP_b14$ | PYEAQELHE | >100 | 20 |
| | $HuP_b15$ | GPLPEHELL | 46.7 | 21 |
| | $HuP_b16$ | GWPLLLEAN | — | 22 |
| | $HuP_b17$ | KGESGFRDR | >100 | 23 |
| | $HuP_b18$ | GSLPRHLFR | 43.8 | 24 |
| | $HuP_b19$ | GPPERLEFR | >100 | 25 |
| High-affinity ligands | $HuP_b20$ | MIYWYSSWL | 0.001 | 1 |
| | $HuP_b21$ | MIYWYSSWI | 0.001 | 2 |
| | $HuP_b22$ | LIYWYSSWL | 0.002 | 3 |
| | $HuP_b23$ | LILYYYYYL | 0.154 | 4 |
| | $HuP_b24$ | LILWYSSWL | 0.002 | 5 |
| | $HuP_b25$ | LLYWWSYSL | — | 6 |
| | $HuP_b26$ | LILWYSSWP | 0.001 | 7 |
| | $HuP_b27$ | LLYWYSSWP | <0.001 | 8 |
| | $HuP_b28$ | MLIYYSSYL | <0.001 | 9 |
| | $HuP_b29$ | FILIYSNLF | 0.002 | 10 |
| | $HuP_b30$ | MIYWYSNWL | <0.001 | 11 |
| | $HuP_b31$ | MIYWYNSWL | <0.001 | 12 |
| | $HuP_b32$ | DIYWYSSWP | <0.001 | 13 |
| | $HuP_b33$ | MIYWYSSWD | 0.001 | 14 |
| | $HuP_b34$ | MIDWYSSWP | 0.001 | 15 |

The affinity of each of these peptides for the HLA-DR2b molecule was measured using the ELISA. All peptides that had the preferred amino acids exhibited a very high affinity ($IC_{50} \leq 0.002$ µM) for HLA-DR2b, except for $HuP_b23$, which exhibited a moderate affinity. In contrast thereto, most of the peptides that had disadvantageous amino acids showed very low ($IC_{50} \geq 30$ µM) or not measurable affinities ($IC_{50}$>100 µM).

2.3 Blocking of the Biological Activity Using High-Affinity HLA-DR2b Peptides

Next, it was to be studied whether the high-affinity HLA-DR2b peptides are capable of blocking the presentation of a myelin-derived antigen on HLA-DR2b in a relevant biological assay. A great number of indications point to a role of the myelin basic protein (MBP) as being an autoantigen in MS. The MBP 83-99 epitope binds selectively to HLA-DR2a and also HLA-DR2b molecules. After stimulation with MBP 85-99, presented on L466 cells that were transfected with HLA-DR2b, large amounts of IL-2 were secreted by the MBP 85-99-specific T-cell-hybridomas 08073.

The ability of the peptides having the highest affinity towards HLA-DR2b to inhibit IL-2 secretion after stimulation of 08073 cells with MBP 85-99 was tested, which is reflected in a decrease in the fluorescence with excitation at 450 nm (optical density, OD). While $HuP_b28$ (SEQ ID No. 9), 31 (SEQ ID No. 12) and 32 (SEQ ID No. 13) significantly reduce IL-2 secretion after stimulation of the MBP 85-99 specific T-cell-hybridomas, $HuP_b27$ (SEQ ID No. 8) and 30 (SEQ ID No. 11) induced only a slight reduction in IL-2 secretion in the peptide concentrations used. $HuP_b17$ (SEQ ID No. 23) and 19 (SEQ ID No. 25), two low-affinity HLA-DR2b peptides, did not show any effect on the IL-2 production in this assay at all; cf. FIG. 1.

The three peptides that showed the strongest effects in the biological assay consisted of sequences that substantially exhibited hydrophobic amino acids. This fact strongly influenced the efficiency of the peptide synthesis, i.e. the amount of peptide that was obtained by means of HPLC purification of the raw peptide fraction following the solid-phase synthesis. Since $HuP_b28$ (SEQ ID No. 9) was synthesized most efficiently, the subsequent studies with respect to the potential of the high-affinity peptides for blocking the autoantigen presentation in vivo were conducted with this peptide.

In order to obtain more structural information on $HuP_b28$ (SEQ ID No. 9), $HuP_b28$-variants were prepared in such a way that all positions in the peptide sequence were substituted by an alanine (A), lysine (K) or X (all possible amino acids except for cysteine (C)), and these peptide variants were tested in the biological assay; cf. FIG. 2.

Substitutions at positions 1 to 5 generally lead to the generation of peptides with an increased capacity for inhibiting IL-2 secretion. Particularly the presence of alanine (A) at position 3 significantly reduces IL-2 secretion. This peptide variant could be of interest, because the substitution of isoleucine (I) against alanine (A) at position 3 of $HuP_b28$ could positively affect the solubility of the peptide and/or the synthesis efficiency. In contrast thereto, alterations at positions 6 to 9 of the peptide usually result in a reduction in the potential of $HuP_b28$ for inhibiting IL-2 secretion.

2.4 Attenuation of the MOG 35-55-Induced EAE in a Mouse Model Using a HLA-DR2-Transgenic Mouse The potential of $HuP_b28$ (SEQ ID No. 9) for attenuating MOG 35-55-induced EAE was then studied in HLA-DR2b-transgenic mice. The co-administration of a high-affinity binding peptide (peptide $HuP_b28$; SEQ ID No. 9) with MOG 35-55 at the time of the immunization reduced the clinical EAE symptoms; cf. FIG. 3.

3. CONCLUSION

The inventors, by using the peptide $HuP_b28$ (SEQ ID No. 9) in HLA-DR1*1501 transgenic mice, by way of example, demonstrated based on MOG 35-55-induced EAE (p<0.05, sum value) that peptide ligands having high affinity towards HLA-DR2b can be used to prevent or even therapeutically treat autoimmune diseases.

---

What is claimed is:

1. A peptide of nine amino acid residues in length which has an amino acid sequence selected from the group consisting of SEQ ID NO:1 to SEQ ID NO:15.

* * * * *

UNITED STATES PATENT AND TRADEMARK OFFICE
CERTIFICATE OF CORRECTION

PATENT NO.       : 8,557,959 B2
APPLICATION NO.  : 12/746098
DATED            : October 15, 2013
INVENTOR(S)      : Weissert et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 532 days.

Signed and Sealed this
Fifteenth Day of September, 2015

Michelle K. Lee
*Director of the United States Patent and Trademark Office*

SEQUENCE LISTING

```
<160> NUMBER OF SEQ ID NOS: 28

<210> SEQ ID NO 1
<211> LENGTH: 9
<212> TYPE: PRT
<213> ORGANISM: Artificial Sequence
<220> FEATURE:
<223> OTHER INFORMATION: High Affinity Binding To HLA-DR26-molecule

<400> SEQUENCE: 1

Met Ile Tyr Trp Tyr Ser Ser Trp Leu
1               5

<210> SEQ ID NO 2
<211> LENGTH: 9
<212> TYPE: PRT
<213> ORGANISM: Artificial Sequence
<220> FEATURE:
<223> OTHER INFORMATION: High Affinity Binding To HLA-DR26-molecule

<400> SEQUENCE: 2

Met Ile Tyr Trp Tyr Ser Ser Trp Ile
1               5

<210> SEQ ID NO 3
<211> LENGTH: 9
<212> TYPE: PRT
<213> ORGANISM: Artificial Sequence
<220> FEATURE:
<223> OTHER INFORMATION: High Affinity Binding To HLA-DR26-molecule

<400> SEQUENCE: 3
```

```
Leu Ile Tyr Trp Tyr Ser Ser Trp Leu
1               5

<210> SEQ ID NO 4
<211> LENGTH: 9
<212> TYPE: PRT
<213> ORGANISM: Artificial Sequence
<220> FEATURE:
<223> OTHER INFORMATION: High Affinity Binding To HLA-DR26-molecule

<400> SEQUENCE: 4

Leu Ile Leu Tyr Tyr Tyr Tyr Tyr Leu
1               5

<210> SEQ ID NO 5
<211> LENGTH: 9
<212> TYPE: PRT
<213> ORGANISM: Artificial Sequence
<220> FEATURE:
<223> OTHER INFORMATION: High Affinity Binding To HLA-DR26-molecule

<400> SEQUENCE: 5

Leu Ile Leu Trp Tyr Ser Ser Trp Leu
1               5

<210> SEQ ID NO 6
<211> LENGTH: 9
<212> TYPE: PRT
<213> ORGANISM: Artificial Sequence
<220> FEATURE:
<223> OTHER INFORMATION: High Affinity Binding To HLA-DR26-molecule

<400> SEQUENCE: 6

Leu Leu Tyr Trp Trp Ser Tyr Ser Leu
1               5

<210> SEQ ID NO 7
<211> LENGTH: 9
<212> TYPE: PRT
<213> ORGANISM: Artificial Sequence
<220> FEATURE:
<223> OTHER INFORMATION: High Affinity Binding To HLA-DR26-molecule

<400> SEQUENCE: 7

Leu Ile Leu Trp Tyr Ser Ser Trp Pro
1               5

<210> SEQ ID NO 8
<211> LENGTH: 9
<212> TYPE: PRT
<213> ORGANISM: Artificial Sequence
<220> FEATURE:
<223> OTHER INFORMATION: High Affinity Binding To HLA-DR26-molecule

<400> SEQUENCE: 8

Leu Leu Tyr Trp Tyr Ser Ser Trp Pro
1               5

<210> SEQ ID NO 9
<211> LENGTH: 9
<212> TYPE: PRT
<213> ORGANISM: Artificial Sequence
<220> FEATURE:
<223> OTHER INFORMATION: High Affinity Binding To HLA-DR26-molecule

<400> SEQUENCE: 9

Met Leu Ile Tyr Tyr Ser Ser Tyr Leu
```

```
<210> SEQ ID NO 10
<211> LENGTH: 9
<212> TYPE: PRT
<213> ORGANISM: Artificial Sequence
<220> FEATURE:
<223> OTHER INFORMATION: High Affinity Binding To HLA-DR26-molecule

<400> SEQUENCE: 10

Phe Ile Leu Ile Tyr Ser Asn Leu Phe
1               5

<210> SEQ ID NO 11
<211> LENGTH: 9
<212> TYPE: PRT
<213> ORGANISM: Artificial Sequence
<220> FEATURE:
<223> OTHER INFORMATION: High Affinity Binding To HLA-DR26-molecule

<400> SEQUENCE: 11

Met Ile Tyr Trp Tyr Ser Asn Trp Leu
1               5

<210> SEQ ID NO 12
<211> LENGTH: 9
<212> TYPE: PRT
<213> ORGANISM: Artificial Sequence
<220> FEATURE:
<223> OTHER INFORMATION: High Affinity Binding To HLA-DR26-molecule

<400> SEQUENCE: 12

Met Ile Tyr Trp Tyr Asn Ser Trp Leu
1               5

<210> SEQ ID NO 13
<211> LENGTH: 9
<212> TYPE: PRT
<213> ORGANISM: Artificial Sequence
<220> FEATURE:
<223> OTHER INFORMATION: High Affinity Binding To HLA-DR26-molecule

<400> SEQUENCE: 13

Asp Ile Tyr Trp Tyr Ser Ser Trp Pro
1               5

<210> SEQ ID NO 14
<211> LENGTH: 9
<212> TYPE: PRT
<213> ORGANISM: Artificial Sequence
<220> FEATURE:
<223> OTHER INFORMATION: High Affinity Binding To HLA-DR26-molecule

<400> SEQUENCE: 14

Met Ile Tyr Trp Tyr Ser Ser Trp Asp
1               5

<210> SEQ ID NO 15
<211> LENGTH: 9
<212> TYPE: PRT
<213> ORGANISM: Artificial Sequence
<220> FEATURE:
<223> OTHER INFORMATION: High Affinity Binding To HLA-DR26-molecule

<400> SEQUENCE: 15

Met Ile Asp Trp Tyr Ser Ser Trp Pro
1               5
```

```
<210> SEQ ID NO 16
<211> LENGTH: 9
<212> TYPE: PRT
<213> ORGANISM: Artificial Sequence
<220> FEATURE:
<223> OTHER INFORMATION: Low Affinity Binding To HLA-DR26-molecule

<400> SEQUENCE: 16

Trp Pro Leu Pro Leu Glu Glu Arg
1               5

<210> SEQ ID NO 17
<211> LENGTH: 9
<212> TYPE: PRT
<213> ORGANISM: Artificial Sequence
<220> FEATURE:
<223> OTHER INFORMATION: Low Affinity Binding To HLA-DR26-molecule

<400> SEQUENCE: 17

Trp Gly Leu Pro Glu His Leu Glu Arg
1               5

<210> SEQ ID NO 18
<211> LENGTH: 9
<212> TYPE: PRT
<213> ORGANISM: Artificial Sequence
<220> FEATURE:
<223> OTHER INFORMATION: Low Affinity Binding To HLA-DR26-molecule

<400> SEQUENCE: 18

Gly Trp Leu Ser Glu Leu Glu Asp Arg
1               5

<210> SEQ ID NO 19
<211> LENGTH: 9
<212> TYPE: PRT
<213> ORGANISM: Artificial Sequence
<220> FEATURE:
<223> OTHER INFORMATION: Low Affinity Binding To HLA-DR26-molecule

<400> SEQUENCE: 19

Pro Phe Pro Ala Pro Thr Arg Glu Gly
1               5

<210> SEQ ID NO 20
<211> LENGTH: 9
<212> TYPE: PRT
<213> ORGANISM: Artificial Sequence
<220> FEATURE:
<223> OTHER INFORMATION: Low Affinity Binding To HLA-DR26-molecule

<400> SEQUENCE: 20

Pro Tyr Glu Ala Gln Glu Leu His Glu
1               5

<210> SEQ ID NO 21
<211> LENGTH: 9
<212> TYPE: PRT
<213> ORGANISM: Artificial Sequence
<220> FEATURE:
<223> OTHER INFORMATION: Low Affinity Binding To HLA-DR26-molecule

<400> SEQUENCE: 21

Gly Pro Leu Pro Glu His Glu Leu Leu
1               5

<210> SEQ ID NO 22
```

```
<211> LENGTH: 9
<212> TYPE: PRT
<213> ORGANISM: Artificial Sequence
<220> FEATURE:
<223> OTHER INFORMATION: Low Affinity Binding To HLA-DR26-molecule

<400> SEQUENCE: 22

Gly Trp Pro Leu Leu Leu Glu Ala Asn
1               5

<210> SEQ ID NO 23
<211> LENGTH: 9
<212> TYPE: PRT
<213> ORGANISM: Artificial Sequence
<220> FEATURE:
<223> OTHER INFORMATION: Low Affinity Binding To HLA-DR26-molecule

<400> SEQUENCE: 23

Lys Gly Glu Ser Gly Phe Arg Asp Arg
1               5

<210> SEQ ID NO 24
<211> LENGTH: 9
<212> TYPE: PRT
<213> ORGANISM: Artificial Sequence
<220> FEATURE:
<223> OTHER INFORMATION: Low Affinity Binding To HLA-DR26-molecule

<400> SEQUENCE: 24

Gly Ser Leu Pro Arg His Leu Phe Arg
1               5

<210> SEQ ID NO 25
<211> LENGTH: 9
<212> TYPE: PRT
<213> ORGANISM: Artificial Sequence
<220> FEATURE:
<223> OTHER INFORMATION: Low Affinity Binding To HLA-DR26-molecule

<400> SEQUENCE: 25

Gly Pro Pro Glu Arg Leu Glu Phe Arg
1               5

<210> SEQ ID NO 26
<211> LENGTH: 266
<212> TYPE: PRT
<213> ORGANISM: Homo sapiens
<220> FEATURE:
<221> NAME/KEY: misc_feature
<223> OTHER INFORMATION: HLA-DR2b

<400> SEQUENCE: 26

Met Val Cys Leu Lys Leu Pro Gly Gly Ser Cys Met Thr Ala Leu Thr
1               5                   10                  15

Val Thr Leu Met Val Leu Ser Ser Pro Leu Ala Leu Ser Gly Asp Thr
            20                  25                  30

Arg Pro Arg Phe Leu Trp Gln Pro Lys Arg Glu Cys His Phe Phe Asn
        35                  40                  45

Gly Thr Glu Arg Val Arg Phe Leu Asp Arg Tyr Phe Tyr Asn Gln Glu
    50                  55                  60

Glu Ser Val Arg Phe Asp Ser Asp Val Gly Glu Phe Arg Ala Val Thr
65                  70                  75                  80

Glu Leu Gly Arg Pro Asp Ala Glu Tyr Trp Asn Ser Gln Lys Asp Ile
                85                  90                  95

Leu Glu Gln Ala Arg Ala Ala Val Asp Thr Tyr Cys Arg His Asn Tyr
```

```
                    100                 105                 110
Gly Val Val Glu Ser Phe Thr Val Gln Arg Val Gln Pro Lys Val
            115                 120                 125

Thr Val Tyr Pro Ser Lys Thr Gln Pro Leu Gln His His Asn Leu Leu
            130                 135                 140

Val Cys Ser Val Ser Gly Phe Tyr Pro Gly Ser Ile Glu Val Arg Trp
145                 150                 155                 160

Phe Leu Asn Gly Gln Glu Glu Lys Ala Gly Met Val Ser Thr Gly Leu
                165                 170                 175

Ile Gln Asn Gly Asp Trp Thr Phe Gln Thr Leu Val Met Leu Glu Thr
                180                 185                 190

Val Pro Arg Ser Gly Glu Val Tyr Thr Cys Gln Val Glu His Pro Ser
            195                 200                 205

Val Thr Ser Pro Leu Thr Val Glu Trp Arg Ala Arg Ser Glu Ser Ala
            210                 215                 220

Gln Ser Lys Met Leu Ser Gly Val Gly Gly Phe Val Leu Gly Leu Leu
225                 230                 235                 240

Phe Leu Gly Ala Gly Leu Phe Ile Tyr Phe Arg Asn Gln Lys Gly His
                245                 250                 255

Ser Gly Leu Gln Pro Thr Gly Phe Leu Ser
                260                 265

<210> SEQ ID NO 27
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: where X1 denotes an amino acid that is selected
      from the group consisting of: leucine, valine, isoleucine,
      methionine, phenylalanine, aspartic acid.
<220> FEATURE:
<221> NAME/KEY: misc_feature
<222> LOCATION: (2)..(2)
<223> OTHER INFORMATION: where X2 denotes an amino acid that is selected
      from the group consisting of isoleucine,leucine, valine.
<220> FEATURE:
<221> NAME/KEY: misc_feature
<222> LOCATION: (3)..(3)
<223> OTHER INFORMATION: where X3 denotes an amino acid that is selected
      from the group consisting of: leucine,isoleucine, methionine,
      tyrosine, aspartic acid.
<220> FEATURE:
<221> NAME/KEY: misc_feature
<222> LOCATION: (4)..(4)
<223> OTHER INFORMATION: where X4 denotes an amino acid that is selected
      from the group consisting of: tyrosine, tryptophan, isoleucine.
<220> FEATURE:
<221> NAME/KEY: misc_feature
<222> LOCATION: (5)..(5)
<223> OTHER INFORMATION: where X5 denotes an amino acid that is selected
      from the group consisting of: tyrosine, phenylalanine, isoleucine,
      tryptophan.
<220> FEATURE:
<221> NAME/KEY: misc_feature
<222> LOCATION: (6)..(6)
<223> OTHER INFORMATION: where X6 denotes an amino acid that is selected
      from the group consisting of: tyrosine, serine, asparagine.
<220> FEATURE:
<221> NAME/KEY: misc_feature
<222> LOCATION: (7)..(7)
<223> OTHER INFORMATION: where X7 denotes an amino acid that is selected
      from the group consisting of tyrosine, serine, asparagine,
      phenylalanine.
<220> FEATURE:
<221> NAME/KEY: misc_feature
```

```
<222> LOCATION: (8)..(8)
<223> OTHER INFORMATION: where X8 denotes an amino acid that is selected
      from the group consisting of: tyrosine, tryptophan, leucine,
      serine.
<220> FEATURE:
<221> NAME/KEY: misc_feature
<222> LOCATION: (9)..(9)
<223> OTHER INFORMATION: where X9 denotes an amino acid that is selected
      from the group consisting of: leucine,isoleucine, valine, proline,
      tyrosine, phenylalanine, aspartic acid.

<400> SEQUENCE: 27

Xaa Xaa Xaa Xaa Xaa Xaa Xaa Xaa Xaa
1               5

<210> SEQ ID NO 28
<211> LENGTH: 24
<212> TYPE: PRT
<213> ORGANISM: Artificial Sequence
<220> FEATURE:
<223> OTHER INFORMATION: synthetic

<400> SEQUENCE: 28

Leu Pro Lys Ser Ala Lys Pro Val Ser Pro Met Arg Met Ala Thr Pro
1               5                   10                  15

Leu Leu Met Arg Pro Ser Met Asp
            20
```